(12) United States Patent
Whiting

(10) Patent No.: US 10,542,998 B2
(45) Date of Patent: *Jan. 28, 2020

(54) LIGATION CLIP WITH FLEXIBLE CLAMPING FEATURE

(71) Applicant: TELEFLEX MEDICAL INCORPORATED, Morrisville, NC (US)

(72) Inventor: Paul E. Whiting, Morrisville, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 176 days.

This patent is subject to a terminal disclaimer.

(21) Appl. No.: 15/241,310

(22) Filed: Aug. 19, 2016

(65) Prior Publication Data

US 2016/0354089 A1    Dec. 8, 2016

Related U.S. Application Data

(63) Continuation of application No. 11/967,733, filed on Dec. 31, 2007, now Pat. No. 9,445,820.

(51) Int. Cl.
*A61B 17/08* (2006.01)
*A61B 17/122* (2006.01)
*A61B 17/00* (2006.01)

(52) U.S. Cl.
CPC .. *A61B 17/122* (2013.01); *A61B 2017/00862* (2013.01)

(58) Field of Classification Search
CPC ................... A61B 17/122; A61B 2017/00862

USPC .................................................. 606/151, 157
See application file for complete search history.

(56) References Cited

U.S. PATENT DOCUMENTS

| 1,728,322 A | 9/1929 | Badrian |
| 3,503,397 A | 3/1970 | Fogarty et al. |
| 3,766,925 A | 10/1973 | Rubricius |
| 3,867,944 A | 2/1975 | Samuels |
| 3,874,042 A | 4/1975 | Eddleman et al. |
| 4,346,869 A | 8/1982 | MacNeill |
| 4,390,019 A | 6/1983 | LeVeen et al. |
| 4,458,682 A | 7/1984 | Cerwin |
| 4,588,160 A | 5/1986 | Flynn et al. |

(Continued)

FOREIGN PATENT DOCUMENTS

GB    2353710 A    3/2001

*Primary Examiner* — Kathleen S Holdwerda
*Assistant Examiner* — Christina C Lauer
(74) *Attorney, Agent, or Firm* — Baker & Hostetler LLP

(57) ABSTRACT

A polymeric surgical ligating clip is provided having curved leg members joined by a resilient hinge. A leg member includes a flexible rib protruding from a vessel clamping inner surface and extends longitudinally between the proximal and distal end portions of the leg member. The flexible rib defines a channel extending transversely through the rib along a majority of said length. The flexible rib can collapse and provides better retention of the clip on a vessel. The clip can contain a flexible rib on both legs in an interlocking fashion. Or a plurality of teeth can protrude from a second vessel clamping inner surface of a second leg member. The plurality of teeth can include first and second rows of teeth extending longitudinally on the second leg member, transversely separated from each other on opposite sides of a centerline of the clip.

23 Claims, 7 Drawing Sheets

(56) References Cited

U.S. PATENT DOCUMENTS

| | | |
|---|---|---|
| 4,638,804 A | 1/1987 | Jewusiak |
| 4,712,549 A | 12/1987 | Peters et al. |
| 4,807,622 A | 2/1989 | Ohkaka et al. |
| 4,822,348 A | 4/1989 | Casey |
| 4,834,096 A | 5/1989 | Oh et al. |
| 4,870,965 A | 10/1989 | Jahanger |
| 4,936,447 A | 6/1990 | Peiffer |
| 4,938,765 A | 7/1990 | Rasmusson |
| 4,942,886 A | 7/1990 | Timmons |
| 4,950,275 A | 8/1990 | Donini |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,160,339 A | 11/1992 | Chen et al. |
| 5,171,251 A | 12/1992 | Bregen et al. |
| 5,171,252 A | 12/1992 | Friedland |
| 5,201,416 A | 4/1993 | Taylor |
| 5,259,405 A | 11/1993 | Hua-Chou |
| 5,279,416 A | 1/1994 | Malec et al. |
| 5,330,487 A | 7/1994 | Thornton et al. |
| 5,462,555 A | 10/1995 | Bolanos et al. |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,697,938 A * | 12/1997 | Jensen ............... A61B 17/122 30/272.1 |
| 5,713,911 A | 2/1998 | Racenet et al. |
| 5,725,542 A | 3/1998 | Yoon |
| 5,810,853 A | 9/1998 | Yoon |
| 5,846,255 A | 12/1998 | Casey |
| 5,908,430 A | 6/1999 | Appleby |
| 5,997,548 A | 12/1999 | Jahanger |
| 6,015,417 A | 1/2000 | Reynolds, Jr. |
| 6,210,419 B1 | 4/2001 | Mayenberger et al. |
| 6,261,303 B1 | 7/2001 | Mayenberger et al. |
| 6,349,727 B1 | 2/2002 | Stewart, Jr. |
| 6,391,035 B1 | 5/2002 | Appleby et al. |
| 6,699,258 B1 | 3/2004 | Sadler et al. |
| 6,719,766 B1 | 4/2004 | Buelna et al. |
| 6,824,547 B2 | 11/2004 | Wilson, Jr. et al. |
| 6,843,253 B2 | 1/2005 | Parkes |
| 6,863,675 B2 | 3/2005 | Wilson, Jr. |
| 6,880,699 B2 | 4/2005 | Gallagher |
| 6,989,017 B2 | 1/2006 | Howell et al. |
| 7,001,412 B2 | 2/2006 | Gallagher et al. |
| 7,052,504 B2 | 5/2006 | Hughett |
| 7,131,977 B2 | 11/2006 | Fowler |
| 7,211,091 B2 | 5/2007 | Fowler et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,963,964 B2 | 6/2011 | Santilli et al. |
| 7,992,757 B2 | 8/2011 | Wheeler et al. |
| 9,445,820 B2 | 9/2016 | Whiting |
| 2003/0074009 A1* | 4/2003 | Ramsey ............... A61B 17/122 606/120 |
| 2004/0059359 A1 | 3/2004 | Wilson |
| 2005/0149069 A1 | 7/2005 | Bertolero et al. |
| 2005/0165422 A1 | 7/2005 | Wilson |
| 2005/0165423 A1* | 7/2005 | Gallagher ............ A61B 17/122 606/151 |
| 2005/0165429 A1 | 7/2005 | Douglas et al. |
| 2007/0276417 A1 | 11/2007 | Mendes, Jr. et al. |
| 2008/0287976 A1 | 11/2008 | Weaner et al. |
| 2009/0012545 A1 | 1/2009 | Williamson et al. |

\* cited by examiner

LIGATION CLIP WITH FLEXIBLE CLAMPING FEATURE

CROSS-REFERENCE TO RELATED APPLICATIONS

This patent application is a continuation application and claims the priority benefit of co-pending U.S. patent application Ser. No. 11/967,733, filed on Dec. 31, 2007, the disclosure of which is hereby incorporated by reference in their entirety.

FIELD OF THE INVENTION

The present invention relates to medical devices and in particular surgical clips for ligation of vessels or tissue.

BACKGROUND OF THE INVENTION

Many surgical procedures require vessels or other tissues of the human body to be ligated during the surgical process. For example, many surgical procedures require cutting blood vessels (e.g., veins or arteries), and these blood vessels may require ligation to reduce bleeding. In some instances, a surgeon may wish to ligate the vessel temporarily to reduce blood flow to the surgical site during the surgical procedure. In other instances a surgeon may wish to permanently ligate a vessel. Ligation of vessels or other tissues can be performed by closing the vessel with a ligating clip, or by suturing the vessel with surgical thread. The use of surgical thread for ligation requires complex manipulations of the needle and suture material to form the knots required to secure the vessel. Such complex manipulations are time-consuming and difficult to perform, particularly in endoscopic surgical procedures, which are characterized by limited space and visibility. By contrast, ligating clips are relatively easy and quick to apply. Accordingly, the use of ligating clips in endoscopic as well as open surgical procedures has grown dramatically.

Various types of hemostatic and aneurysm clips are used in surgery for ligating blood vessels or other tissues to stop the flow of blood. Such clips have also been used for interrupting or occluding ducts and vessels in particular surgeries such as sterilization procedures. Typically, a clip is applied to the vessel or other tissue by using a dedicated mechanical instrument commonly referred to as a surgical clip applier, ligating clip applier, or hemostatic clip applier. Generally, the clip is left in place after application to the tissue until hemostasis or occlusion occurs.

Ligating clips can be classified according to their geometric configuration (e.g., symmetric clips or asymmetric clips), and according to the material from which they are manufactured (e.g., metal clips or polymeric clips). Symmetric clips are generally "U" or "V" shaped and thus are substantially symmetrical about a central, longitudinal axis extending between the legs of the clip. Symmetric clips are usually constructed from metals such as stainless steel, titanium, tantalum, or alloys thereof. But, with the advent of high technology diagnostic techniques using computer tomography (CATSCAN) and magnetic resonance imaging (MM), metallic clips have been found to interfere with the imaging techniques. To overcome such interference limitations, biocompatible polymers have been increasingly used for surgical clips.

Some well known polymeric clips are disclosed in U.S. Pat. No. 4,834,096 to Oh et al. and U.S. Pat. No. 5,062,846 to Oh et al., both of which are commonly owned with the assignee of the present invention, the disclosures of which are herein incorporated by reference in their entirety. These plastic clips generally comprise a pair of curved legs joined at their proximal ends with an integral hinge or heel.

Although plastic ligating clips are well known in the surgical area and improvements have been made to the ligating clips, including providing protrusions on the inner surfaces of the leg members to impede the lateral movement of a vessel during clip closure (see, for example, the aforementioned U.S. Pat. Nos. 4,834,096 and 5,062,846), these improvements have been less effective in preventing movement of the clip along the length of a vessel or tissue during and after clip closure. One potential improvement in this area is disclosed in commonly-owned U.S. Patent Application Pub. No. 2005/0165423 A1 by Gallagher et al., the disclosure of which is incorporated by reference in its entirety, which discloses a polymeric surgical clip having an interlocking tongue-in-groove mechanism formed by a lip or tongue protruding from a portion of the inner surface of one leg and a groove formed in a corresponding portion of the inner surface of the other leg; or a lock-step mechanism, formed by complementary L-shaped notches wherein a notch is provided in a portion of the inner surface of each leg. The interlocking mechanisms act to impede movement of the clip relative to the vessel being clamped.

In all of the known ligating clips however, there remains a need to improve the effectiveness of clamping about a vessel, while minimizing the damage to the vessel and surrounding tissue. The occlusion of the vessel by a ligating clip can accidentally damage the vessel or severe it. Therefore, a ligating clip must have a sufficient degree of clamping force and retention on a vessel, so as not to move relative to the vessel when applied, while also preserving tissue integrity and minimizing damage. Accordingly, there is a need to provide an improved surgical ligating clip with that serves to secure the tissue or vessel engaged by the clip, while robustly remaining attached to the vessel with a minimum level of damage to tissue.

SUMMARY OF THE INVENTION

The foregoing needs are met, to a great extent, by the present invention, wherein in one aspect a ligation clip is provided that includes a flexible collapsible rib extending along an inner vessel clamping surface of one or both of the legs of the clip, providing for better, safer, and more robust retention of the clip on the vessel. A single flexible rib on one leg can be used with a plurality of protrusions or teeth disposed on the opposite leg, defining an interlocking mechanism for improved vessel clamping and retention. The present invention can apply additional pressure on the vessel tissue through a cross-clamping action as well as applying pressure normal to the tissue. These provide a tortuous path or surface for the vessel tissue and increase the area of the tissue being retained.

In accordance with one embodiment of the present invention, a ligating clip is provided, including first and second curved leg members having respective proximal and distal end portions. The proximal end portions are joined by a resilient hinge. The first and second curved leg members have respective first and second vessel clamping inner surfaces facing each other when the first and second leg members are moved from an open position to a closed position about the hinge. The first leg member has a flexible rib protruding from the first vessel clamping inner surface and extending longitudinally a length between the proximal and distal end portions of the first leg member. The flexible rib defines a channel extending transversely through the rib along a majority of said length.

In accordance with another aspect of the present invention, a ligating clip defining a longitudinal length of said clip is provided, including two leg members having respective proximal and distal end portions. The proximal end portions are joined by a resilient hinge. The two leg members have respective vessel clamping inner surfaces facing each other when the two leg members are moved from an open position to a closed position about the hinge. At least one flexible rib is included on at least one of said leg members and extends along a vessel clamping inner surface of said at least one leg member along a majority of a longitudinal span of said vessel clamping inner surface. The at least one flexible rib includes a longitudinal span member spaced from the rest of said at least one leg member. The longitudinal span member is connected to said at least one leg member at the respective proximal and distal end portion of said leg member.

In accordance with yet another aspect of the present invention, a ligating clip is provided, having first and second curved leg members having respective proximal and distal end portions. The proximal end portions are joined by a resilient hinge. The first and second curved leg members have respective first and second vessel clamping inner surfaces facing each other when said first and second leg members are moved from an open position to a closed position about said hinge. The first leg member has a first flexible rib protruding from said first vessel clamping inner surface and extending longitudinally a first length between the proximal and distal end portions of the first leg member. The first flexible rib defines a first channel extending transversely through the first rib along a majority of said first length. The second leg member includes a second collapsible, flexible rib protruding from said second vessel clamping inner surface and extending longitudinally a second length between the proximal and distal end portions of the second leg member. The second flexible rib defines a second channel extending transversely through said second rib along a majority of said second length.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
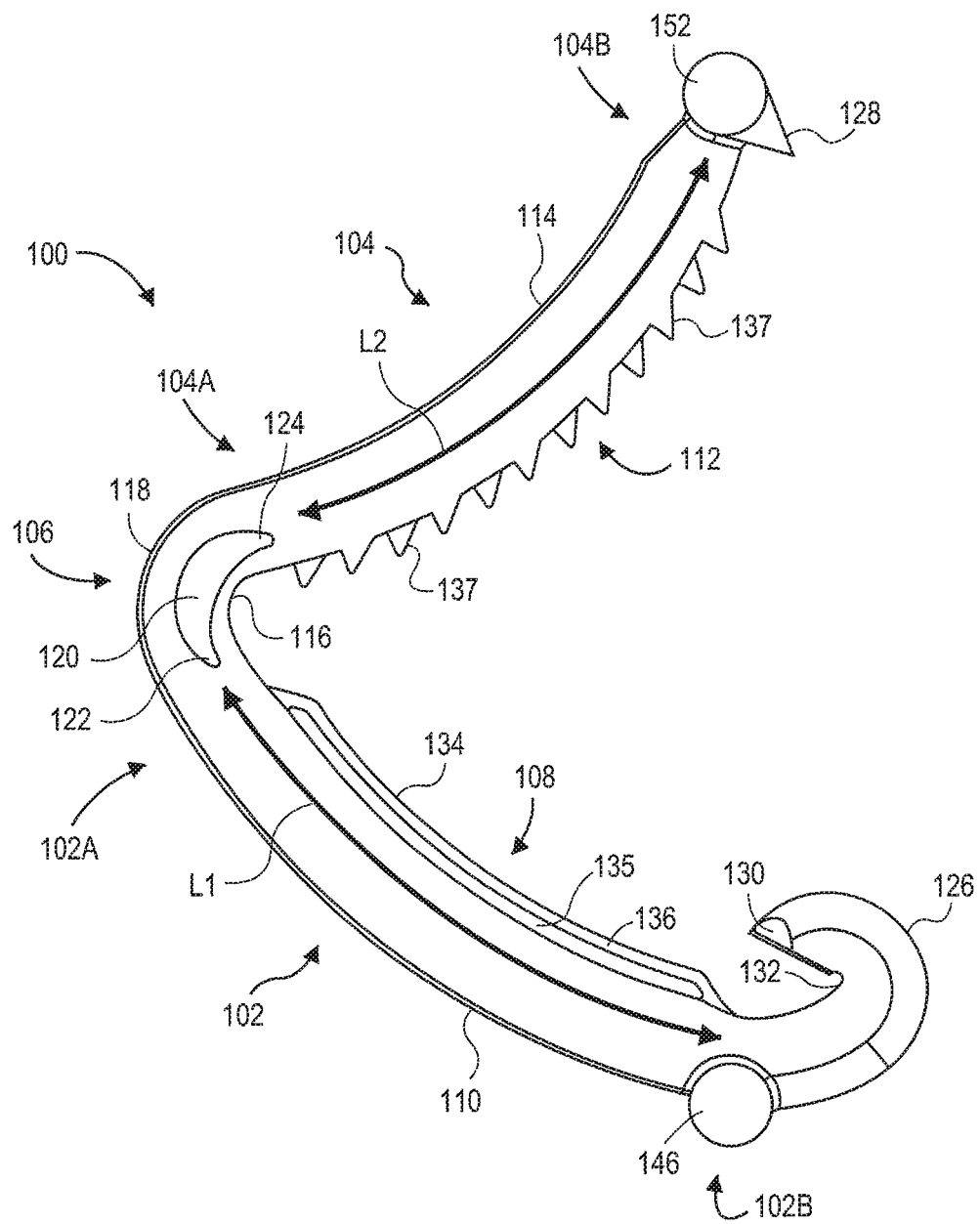
FIG. 1 is an enlarged side elevation view of one embodiment of a surgical ligating clip of the present invention.

The invention will now be described with reference to the drawing figures, in which like reference numerals refer to like parts throughout. In accordance with conventional practice, as used herein, and unless otherwise indicated herein, the term "proximal" or "proximal end" shall refer to the specified end of a device or its component which is generally closer to the medical personnel handling or manipulating the device as it is intended to be used, and the term "distal" or "distal end" shall refer to the specified end of a device or its component which is opposite the proximal end.

The present invention involves a surgical ligating clip, preferably made of a polymeric material, which can be used to clamp vessels such as arteries in the body, having a pair of asymmetric, curved concave-convex legs, and including one or more flexible rib portions as well as rows of protruding teeth to provide an improved and superior interlocking means to retain the clip on a vessel. The surgical clip of the present invention includes one or more flexible ribs to apply additional pressure on the tissue of the vessel being ligated, and can additionally provide a cross-clamping action as well as applying pressure normal to the tissue. Additional features of the present invention include exaggerated teeth on either side of the centrally located flexible ribs, which provides a tortuous path and surface for the tissue and increases the area of the tissue being retained by the clip.

Figure 2:
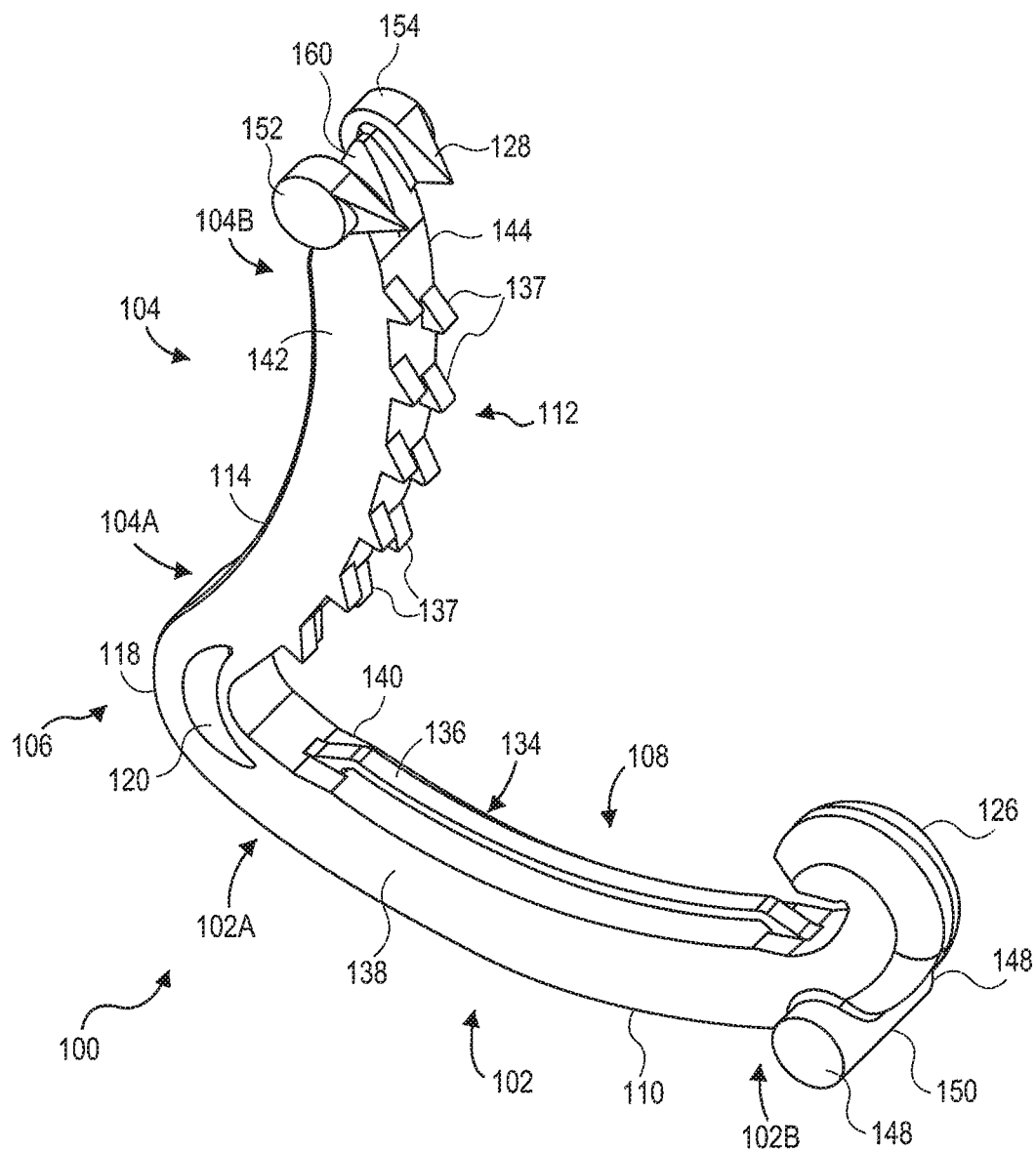
FIG. 2 is an enlarged perspective view of the embodiment of FIG. 1.
Figure 3:
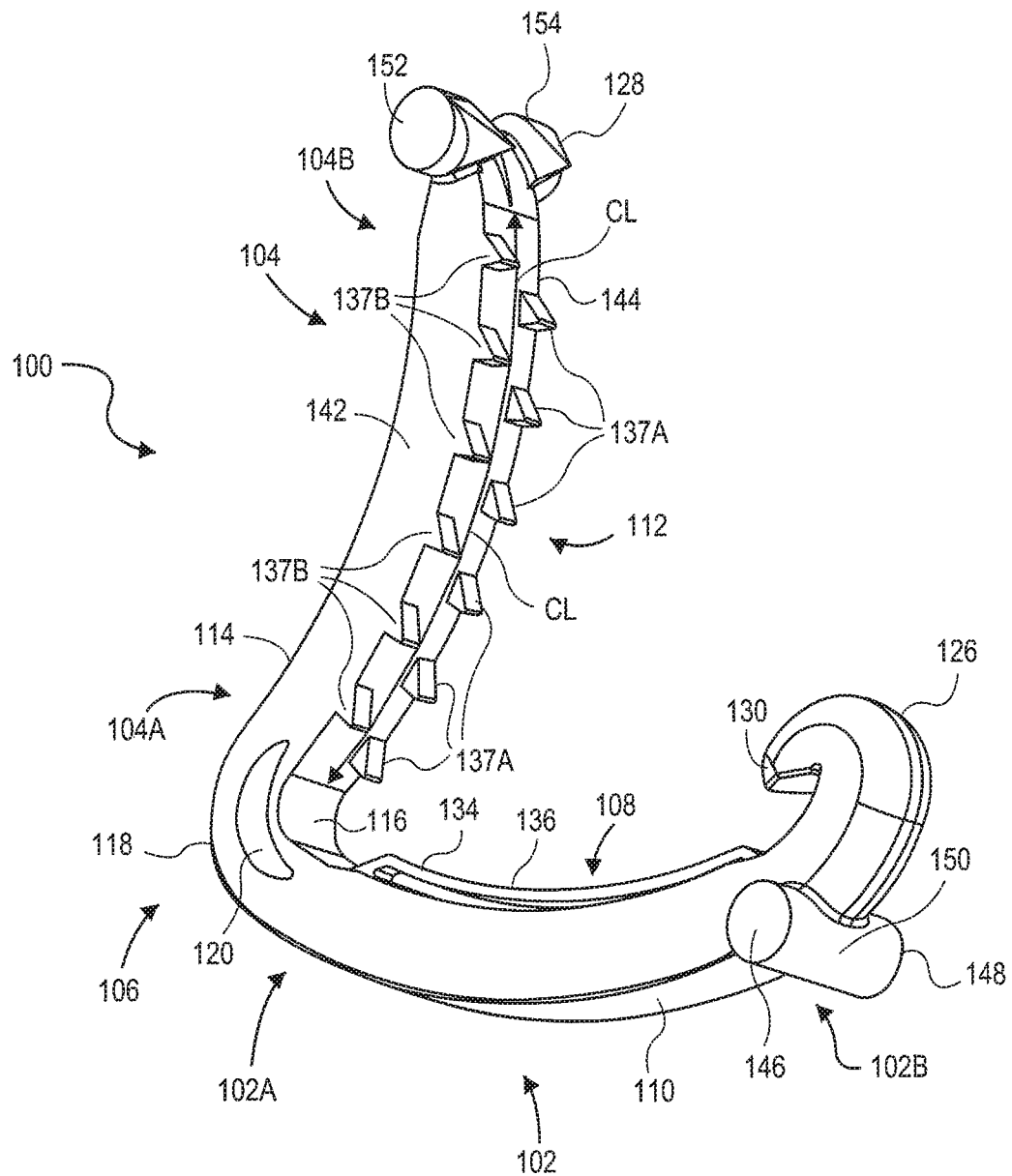
FIG. 3 is another enlarged perspective view of the embodiment of FIG. 1.

FIG. 1 is an enlarged side elevation view of one embodiment of a surgical ligating clip of the present invention, designated generally as 100. FIG. 2 and FIG. 3 show alternative perspective view of the surgical clip 100. Clip 100 and others of similar design are particularly useful as hemostatic clips that can be latched around a vessel or other type of tissue to ligate the vessel and thereby stop or reduce the flow of fluid through the vessel.

The body of clip 100 includes a first leg member 102 having a proximal end portion 102A and distal end portion 102B, and a second leg member 104 having a proximal end portion 104A and distal end portion 104B. As used herein, the term "longitudinal" and a "longitudinal" direction or span shall mean the dimension along clip 100 or legs 102 or 104 which extends along the length of said legs from their respective proximal end portions 102A, 104A to their respective distal end portions 102B, 104B, as would be commonly understood by one of skill in the art, and as shown in FIG. 1 as longitudinal axes L1 and L2. Furthermore, as used herein, the "transverse" direction shall be any axis or direction which is orthogonal of longitudinal axes L1 and L2, which would be normal to the plane of view in FIG. 1.

First and second legs 102 and 104 are joined at their proximal ends by an integral resilient hinge section, generally designated 106. First and second legs 102 and 104 are curved and have complementary arcuate profiles, and include respective inner vessel clamping surfaces. Thus, as best shown in FIG. 1, first leg 102 has a concave inner vessel clamping surface 108 and a convex outer surface 110, and second leg 104 has a convex inner vessel clamping surface 112 and a concave outer surface 114. Convex inner surface 112 of second leg 104 and concave inner surface 108 of first leg 102 have substantially matching radii of curvature.

Hinge section 106 has a continuous concave inner surface 116 and a continuous convex outer surface 118. Concave inner surface 116 of hinge 106 joins concave inner surface 108 of first leg 102 and convex inner surface 112 of second leg 104. Convex outer surface 118 of hinge section 106 joins convex outer surface 110 of first leg 102 and concave outer surface 114 of second leg 104. Curved slot 120 is located between curved hinge surfaces 116 and 118, and is positioned closer to inner surface 116 than to outer surface 118. Slot 120 extends completely through hinge section 106 from side to side and its opposite ends 122, 124 extend into the proximal ends of first and second legs 102 and 104, respectively. Slot 120 provides added flexibility and resiliency to hinge section 106, but the inner concave surface 116 prevents any portion of a clamped vessel from being trapped within slot 120.

First leg 102 transitions to a curved, C-shaped hook section 126 at its distal end. Second leg 104 transitions to a pointed tip section 128 at its distal end. The distal portion of hook section 126 curves inwardly and points generally toward inner surface 116 of hinge 106. The hook section 126 has a transverse beveled surface 130 and a concave inner surface which mates with concave inner surface 108 to define a latching recess 132. The latching recess 132 is adapted for conformally engaging tip section 128 in the course of compressing clip 100 into a latched or locked position around a vessel or other tissue.

Clip 100 further includes a flexible rib 134 disposed on the first vessel clamping inner surface 108 on the first leg member 102. Flexible rib 134 protrudes from said first leg member 102 and extends longitudinally a length between the proximal 102A and distal 102B end portions of the first leg member 102. The flexible rib 134 defines a channel 135 which extends transversely through said rib 134 along a majority of the length of the rib 134. In the embodiment of FIGS. 1 through 3, the channel 135 stretches along a majority of the overall longitudinal length of the rib 134, but it is understood that said channel 135 can also accommodate varying arrangements including one or more discrete transverse channels through the rib 134, located at varying positions and longitudinal spans along the rib 134.

Clip 100 can be constructed from any suitable biocompatible material, such as certain metals and polymers. However, the present invention is particularly suitable for practice with polymeric clips. Thus, clip 100 preferably comprises a one-piece integral polymeric body formed from a suitable strong biocompatible engineering plastic such as the type commonly used for surgical implants. Examples include polyethylene terephthalate (PET), polybutylene terephthalate (PBT), polyoxymethylene, or other thermoplastic materials having similar properties that can be injection-molded, extruded or otherwise processed into like articles.

Figure 6:
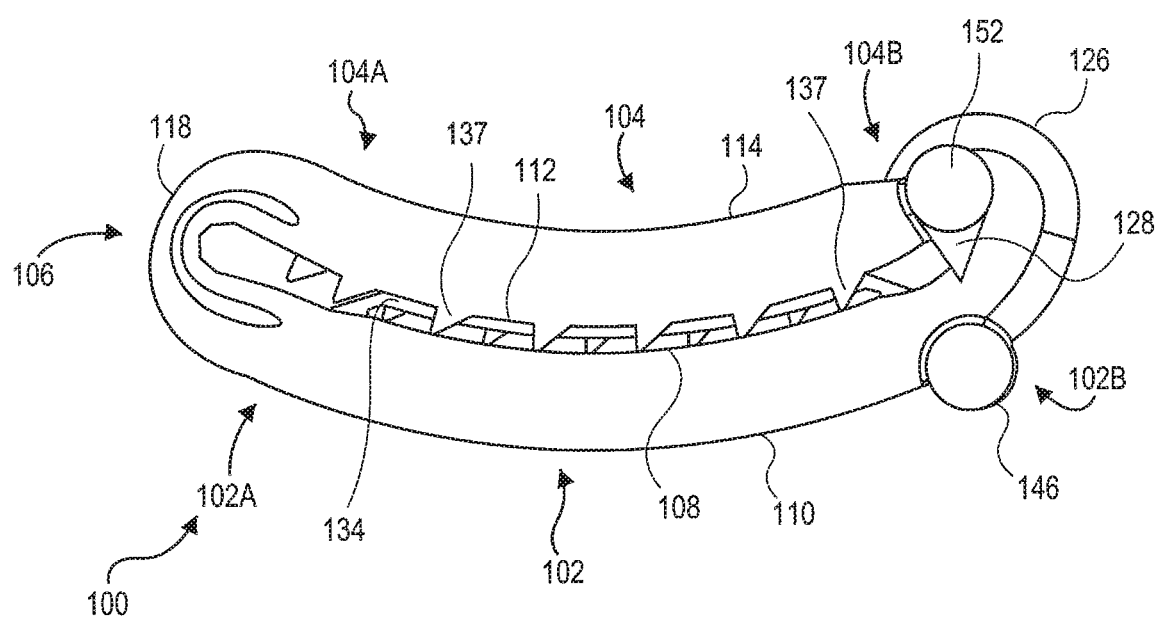
FIG. 6 is an enlarged side elevation view of the surgical ligating clip in FIGS. 1-3 in a closed position.

In the embodiment shown in FIGS. 1-3, flexible rib 134 includes a longitudinal span member 136 spaced from the rest of the leg member 102 by virtue of the channel 135 therebetween. The longitudinal span member 136 is connected to leg member 102 at the respective proximal 102A and distal 102B end portions of said leg member, as best shown in FIG. 1. This particular structural configuration of flexible rib 134 renders it somewhat collapsible, such that, upon closure of the clip 100 around a vessel, the rib 134 will flex and collapse towards the leg 102 and more effectively grip and retain tissue, while minimizing potential damage to said tissue. FIG. 6 is an enlarged side elevation view of the surgical ligating clip in FIGS. 1-3 in a closed position.

In the embodiment shown in FIGS. 1-3, the clip 100 can include a plurality of teeth 137 protruding on the second vessel clamping inner surface 112 on the second leg member 104. As best shown in FIG. 3, the plurality of teeth 137 include first 137A and second 137B rows of teeth extending longitudinally between the proximal 104A and distal 104B end portions of the second leg member 104, the first row 137A being transversely separated from the second row 137B on opposite sides of a centerline CL of the second vessel clamping inner surface 112. The centerline CL is also coincident with a centerplane of symmetry of the clip 100, said centerplane spanning the direction of longitudinal axes L1 and L2 (and parallel to the view of FIG. 1) and dividing clip 100 into symmetric halves with the exception of the longitudinal staggering of tooth rows 137A and 137B as best shown in FIG. 3. The transverse separation of tooth rows 137A and 137B about centerline CL is just enough, or slightly greater, than the transverse width of flexible rib 134 and its longitudinal span member 136, as best shown in FIG. 2. Flexible rib 134 is approximately centered between side surfaces 138 and 140 of first leg member 102 such that flexible rib 134 is also positioned on a centerline of vessel clamping surface 108 of first leg 102, which centerline is also coincident with the centerplane of the clip 100 and mates with the centerline CL of surface 112 on second leg 104, such that when the clip 100 is closed about a vessel, the flexible rib 134 fits into the transverse separation between rows of teeth 137A and 137B, providing a tortuous path or surface for tissue being clamped, and increasing the effective area of tissue being retained by clip 100 over the prior art, as well as increasing the effective pressure being applied to the tissue by clip 100.

As shown in the embodiment of FIGS. 1-3, because first leg member 102 has a concave radius of curvature, viewed relative to facing the first vessel clamping inner surface 108, and the second leg member 104 has a convex radius of curvature, viewed relative to facing the second vessel clamping inner surface 112, the length of flexible rib 134 also has a concave radius of curvature when facing the first vessel clamping inner surface 108, such that the closure of clip 100 results in the various radii of curvature mating to effectively close the clip 100 over a vessel. The combination of flexible rib 134 and transversely separated rows of teeth 137A and 137B on respective first and second vessel clamping inner surfaces 108 and 112 form an interlocking mechanism which provides improved, robust, flexible, and safer vessel retention by a ligating clip over the prior art.

Adjacent to the distal end of the first leg 102 and immediately inward of hook section 126, cylindrical bosses 146 and 148 protrude perpendicular to each of the opposed side surfaces 138 and 140. In the illustrated example of clip 100, a bridge section 150 couples bosses 146 and 148 together. As evident in FIGS. 1-3, bosses 146 and 148 project outwardly beyond convex outer surface 110 of first leg 102. At the distal end of second leg 104, cylindrical bosses 152 and 154 protrude perpendicular to each of the opposed side surfaces 142 and 144 of second leg 104 and extend longitudinally forward beyond the point of tip 128.

In the practice of ligating a vessel as understood by persons skilled in the art, clip 100 is designed to be compressed into a latched or locked position around the vessel through the use of an appropriate clip applicator instrument, such as a type described in U.S. Pat. No. 5,100,416. The clip applicator instrument engages bosses 146, 148, 152 and 154 of clip 100 and pivots bosses 146, 148, 152 and 154 inwardly about hinge section 106. This causes first and second legs 102 and 104 to close around the vessel, with convex inner surface 112 of second leg 104 and complementary concave inner surface 108 of first leg 102 contacting the outer wall of the vessel. Flexible rib 134 pushes a portion of the vessel into the transverse spacing between tooth rows 137A and 137B, where the clamping pressure also pushes portions of the vessel into the longitudinal spacing between teeth on the two rows 137A and 137B, all of which effectively secures the clip 100 to the vessel and prevents movement of the clip or vessel during or after clip closure. Tip section 128 of second leg 104 also contacts hook section 126. Pivotal movement by the applicator instrument longitudinally elongates first leg 102 and deflects hook section 126, allowing tip section 128 to align with latching recess 132. The hook member 126 can terminates in a sharp pointed tip at the convergence of beveled surface 130, which extends toward the proximal end portion 102A of first leg member 102. The distal end of said second leg member 104 includes a groove 160 through which said sharp pointed tip 130 passes when the leg members 102 and 104 are moved to the closed position about a vessel. Upon release of the applicator instrument, tip section 128 and groove 160 snaps into and is conformably seated in latching recess 132 inside hook 126, at which point clip 100 is in its latched condition and the vessel securely engaged thereby.

Figure 4:
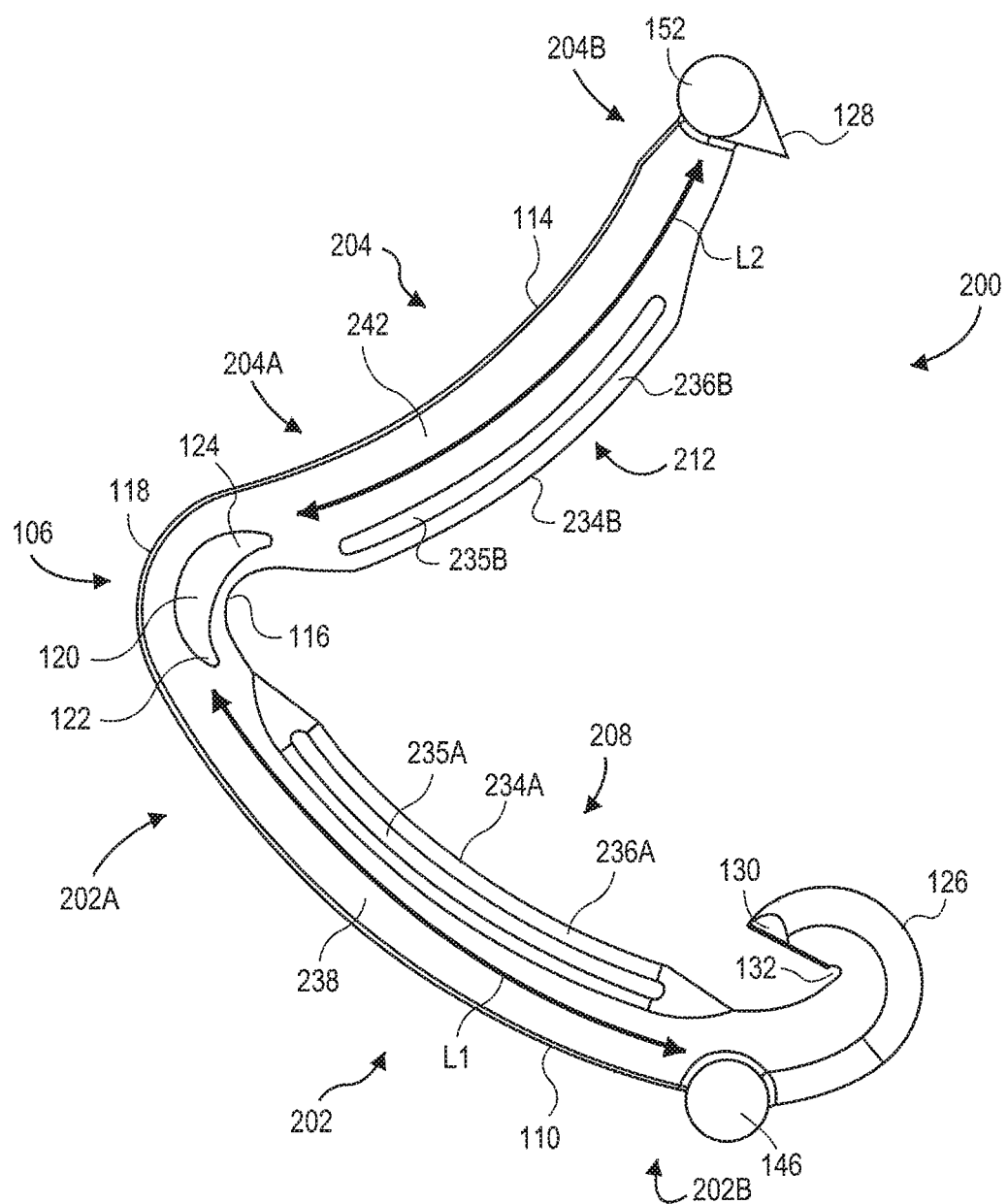
FIG. 4 is an enlarged side elevation view of another embodiment of a surgical ligating clip of the present invention.
Figure 5:
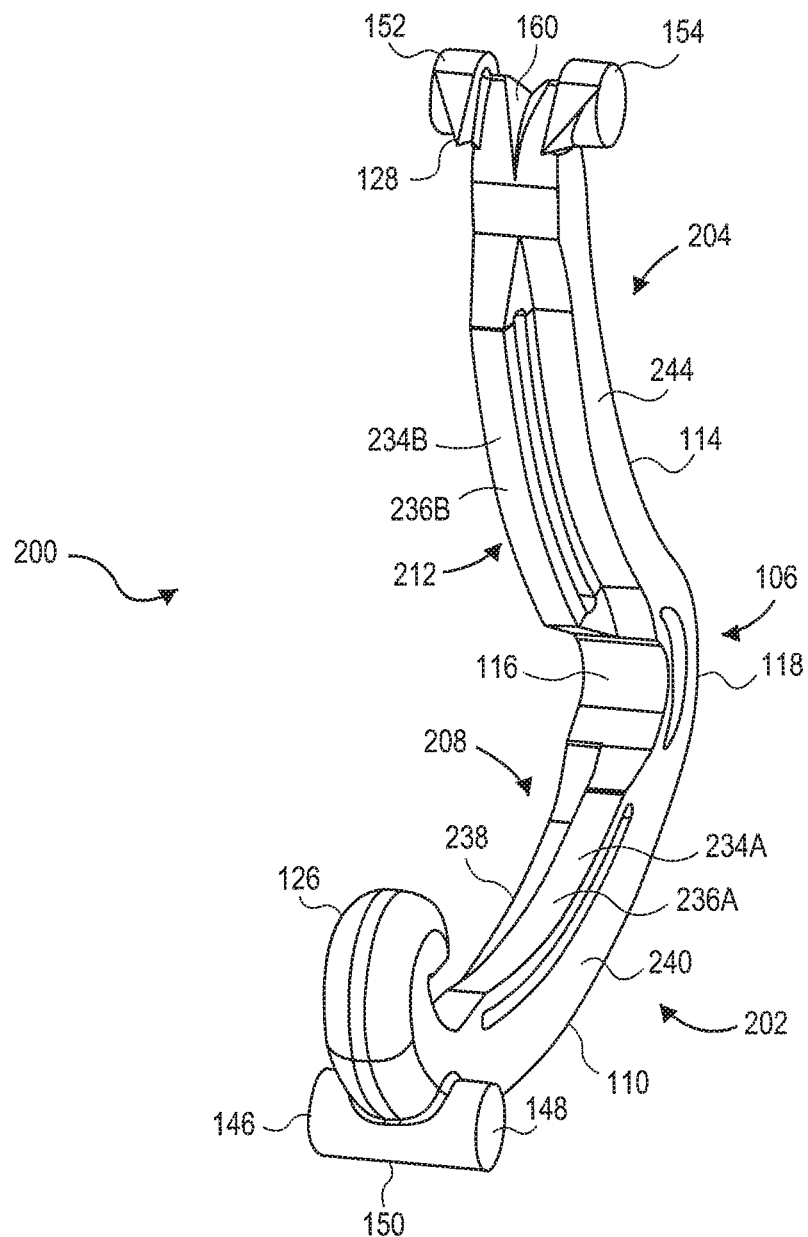
FIG. 5 is an enlarged perspective view of the embodiment of FIG. 4.

FIGS. 4-5 depict an alternate embodiment of an asymmetric surgical clip 200 in accordance with the invention. Clip 200 bears many similarities to clip 100 described above with reference to FIGS. 1-3. For example, the materials and procedures used to make and apply clip 100 may be used to make and apply clip 200 as well. Similarly, the various features of clip 100 described above are referenced where appropriate in FIGS. 4-5 with respect to clip 200 using the same reference numerals used in FIGS. 1-3.

FIG. 4 is an enlarged side elevation view of clip 200. The body of clip 200 includes a first leg 202 having a proximal end portion 202A and distal end portion 202B, and a second leg 204 having a proximal end portion 204A and a distal end portion 204B. First and second legs 202 and 204 are joined at their proximal ends by integral hinge section 106. First and second legs 202 and 204 are curved and have complementary arcuate profiles. Thus, first leg 202 has a concave vessel clamping inner surface 208 and a convex outer surface 110, and second leg 104 has a convex vessel clamping inner surface 212 and a concave outer surface 114. Convex inner surface 212 of second leg 104 and concave inner surface 208 of first leg 202 have substantially matching radii of curvature.

Hinge section 106 has a continuous concave inner surface 116 and a continuous convex outer surface 118. Concave inner surface 116 of hinge 106 joins concave inner surface 208 of first leg 202 and convex inner surface 212 of second leg 204. Convex outer surface 118 of hinge section 106 joins convex outer surface 110 of first leg 102 and concave outer surface 114 of second leg 104. Curved slot 120 is located between curved hinge surfaces 116 and 118, and is positioned closer to inner surface 116 than to outer surface 118. Slot 120 extends transversely completely through hinge section 106 from side to side and its opposite ends 122, 124 extend into the proximal ends of first and second legs 202 and 204, respectively. Slot 120 provides added flexibility and resiliency to hinge section 106, but the inner concave surface 116 prevents any portion of a clamped vessel from being trapped within slot 120.

First leg 202 transitions to a curved, C-shaped hook section 126 at its distal end. Second leg 204 transitions to a pointed tip section 128 at its distal end. The distal portion of hook section 126 curves inwardly and points generally toward inner surface 116 of hinge 106. The hook section 126 has a transverse beveled surface 130 and a concave inner surface which mates with concave inner surface 208 to define a latching recess 132. The latching recess 132 is adapted for conformally engaging tip section 128 in the course of compressing clip 200 into a latched or locked position around a vessel or other tissue.

As best shown in FIG. 5, clip 200 further includes two flexible ribs 234A and 234B, one each disposed on the respective first vessel clamping inner surface 208 on first leg member 202 and second vessel clamping inner surface 212 on the second leg member 204. Flexible ribs 234A and 234B protrude from respective first leg member 202 and second leg member 204 and extend longitudinally a length between the respective proximal 202A, 204A and distal 202B, 204B end portions of leg members 202, 204. The flexible ribs 234A and 234B each defines a respective channel 235A and 235B which extend transversely through said ribs 234A and 234B along a majority of the length of said ribs. In the embodiment of FIGS. 4-5, the channels 235A and 235B stretch along a majority of the overall longitudinal length of the ribs 234A and 234B, but it is understood that said channels 235A and 235B can also accommodate varying arrangements including one or more discrete transverse channels through each rib 234A and 234B, located at varying positions and longitudinal spans along said ribs. Alternatively, one of channels 235A or 235B can be missing such that one of ribs 234A or 234B is solid instead of hollow. Clip 200 can be constructed from any suitable biocompatible material, such as certain metals and polymers, such as previously discussed above with Clip 100.

The ribs 234A and 234B form complementary parts of an interlocking mechanism. In this embodiment, the complementary parts are arranged in a lock-step, or scissor-like configuration. In the embodiment shown in FIGS. 4-5, flexible ribs 234A and 234B each include a respective longitudinal span member 236A and 236B spaced from the rest of their respective leg members 202 and 204 by virtue of the respective channels 235A and 235B therebetween. The longitudinal span members 236A and 236B are each connected to their respective leg members 202 and 204 at the respective proximal 202A, 204A and distal 202B, 204B end portions of said leg members, as best shown in FIG. 4. This particular structural configuration of flexible ribs 234A and 234B renders said ribs somewhat collapsible, such that, upon closure of the clip 200 around a vessel, each rib 234A and 234B will flex and collapse towards their respective attached legs 202 and 204 and more effectively grip and retain tissue, while minimizing potential damage to said tissue.

As shown in FIG. 5, the first flexible rib 234A is disposed on a first side of the clip 200, and the second flexible rib 234B is disposed on a second side of the clip 200 opposite the first side. The ribs 234A and 234B are thus offset of opposite of the longitudinal centerplane of the clip 200, creating the complementary parts of a scissor-like interlocking mechanism for ligating and retaining a vessel around which clip 200 is clamped. As shown in FIGS. 4-5, the first flexible rib 234A has a concave radius of curvature when facing the vessel clamping inner surface 208, and the second flexible rib 234B has a convex radius of curvature when facing the vessel clamping inner surface 212.

Adjacent to the distal end of the first leg 202 and immediately inward of hook section 126, cylindrical bosses 146 and 148 protrude perpendicular to each of the opposed side surfaces 238 and 240. In the illustrated example of clip 200, a bridge section 150 couples bosses 146 and 148 together. As evident in FIGS. 4-5, bosses 146 and 148 project outwardly beyond convex outer surface 110 of first leg 202. At the distal end of second leg 204, cylindrical bosses 152 and 154 protrude perpendicular to each of the opposed side surfaces 242 and 244 of second leg 204 and extend longitudinally forward beyond the point of tip 128.

Figure 7:
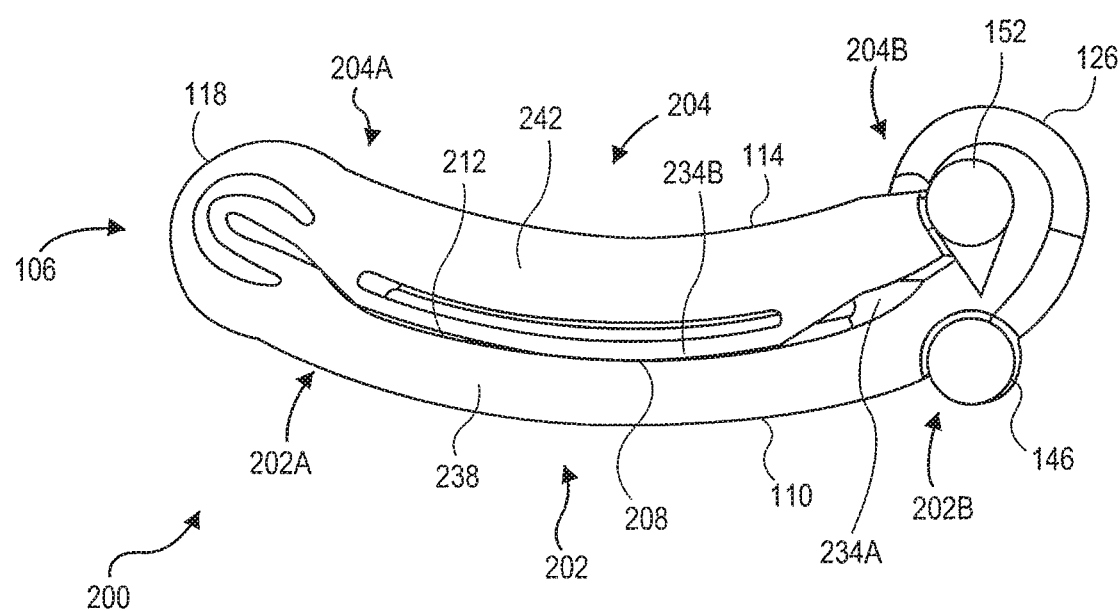
FIG. 7 is an enlarged side elevation view of the surgical ligating clip in FIGS. 4-5 in a closed position.

In the practice of ligating a vessel as understood by persons skilled in the art, clip 200 is designed to be compressed into a latched or locked position around the vessel through the use of an appropriate clip applicator instrument, in much the same manner as described above with respect to clip 100. In clip 200 however, instead of a single flexible rib on one leg fitting into rows of teeth disposed on the opposite leg as in clip 100, the two flexible ribs 234A and 234B interlock together to provide a cross-clamping action as well as additional pressure applied normal to tissue on a vessel. FIG. 7 shows the clip 200 in a closed position.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip for ligating a vessel, the clip comprising:
    first and second curved leg members having respective proximal and distal end portions, the proximal end portions being joined by a hinge,
    a flexible rib on the first curved leg member extending longitudinally along a length from the proximal end portion to the distal end portion of the first curved leg member, the flexible rib being attached spaced from the first curved leg member via at least two attachment portions to define a channel extending transversely between the flexible rib and the first curved leg member,
    a first pair of bosses extending transversely from opposite sides of the distal end portion of the first curved leg member, and a second pair of bosses extending transversely from opposite sides of the distal end portion of the second curved leg member, and
    first and second rows of teeth extending longitudinally on a vessel clamping inner surface of the second curved leg member, the first and second rows of teeth being transversely separated from each other on opposite sides of a centerline of the vessel clamping inner surface,
    wherein the flexible rib is received between the first and second rows of teeth in a closed configuration.

2. The clip of claim 1, wherein the first curved leg member terminates at a distal end in a hook member curved toward the second curved leg member, the second curved leg member terminates at a distal end in a complimentary locking portion to the hook member, and the hook member is configured to deflect about the distal end of the second curved leg member to lock the clip in the closed configuration when the first and second curved leg members are moved to the closed configuration.

3. The clip of claim 2, wherein the hook member terminates in a sharp pointed tip extending toward the proximal end portion of the first curved leg member, and the distal end of the second curved leg member includes a groove through which the sharp pointed tip passes when the first and second curved leg members are moved to the closed configuration.

4. The clip of claim 1, wherein the hinge is integral to the first and second curved leg members, the hinge is resilient, and the hinge includes a continuous concave inner surface and a continuous convex outer surface.

5. The clip of claim 1, wherein the teeth of the first row of teeth are longitudinally separated from each other along the vessel clamping inner surface, and the teeth of the second row of teeth are longitudinally separated from each other along the vessel clamping inner surface.

6. The clip of claim 1, wherein the first and second rows of teeth are staggered along the vessel clamping inner surface.

7. The clip of claim 1, wherein the first and second curved leg members have matching radii of curvature.

8. The clip of claim 1, wherein each of the first and second curved leg members has a curvature extending from the respective proximal end portion to the respective distal end portion.

9. The clip of claim 1, wherein the vessel clamping inner surface of the second curved leg member has a convex radius of curvature facing the first curved leg member, and a vessel clamping inner surface of the first curved leg member has a concave radius of curvature facing the second curved leg member.

10. A clip for ligating a vessel, the clip comprising:
    first and second curved leg members having respective proximal and distal end portions, the proximal end portions being joined by a hinge, and
    at least one flexible rib on the first curved leg member, the at least one flexible rib extending longitudinally along a length from the proximal end portion to the distal end portion of the first curved leg member, the flexible rib being attached spaced from the first curved leg member via at least two attachment portions to define a channel extending transversely between the flexible rib and the first curved leg member, and
    first and second rows of teeth extending longitudinally on a vessel clamping inner surface of the second curved leg member, the first and second rows of teeth being transversely separated from each other on opposite sides of a centerline of the vessel clamping inner surface,
    wherein the at least one flexible rib is received between the first and second rows of teeth in a closed configuration,
    wherein the clip is configured to be independently retained without use of any external applier or tool on the vessel after the clip is applied to occlude the vessel,
    wherein the second curved leg member terminates at its distal end in a hook member curved toward the first curved leg member, the first curved leg member terminates at its distal end in a complimentary locking portion to the hook member, and the hook member is configured to deflect about the distal end of the first curved leg member to lock the clip in the closed configuration when the first and second curved leg members are moved to the closed configuration, and wherein the hook member terminates in a sharp pointed tip extending toward the proximal end portion of the second curved leg member, and the distal end of the first curved leg member includes a groove through which the sharp pointed tip passes when the first and second curved leg members are moved to the closed configuration.

11. The clip of claim 10, wherein the first and second curved leg members have respective first and second vessel clamping inner surfaces.

12. The clip of claim 10, wherein the first curved leg member has a convex radius of curvature facing the second curved leg member, and the second curved leg member has a concave radius of curvature facing the first curved leg member.

13. The clip of claim 10, further comprising:
a first pair of bosses extending transversely from opposite sides of the distal end portion of the first curved leg member, and
a second pair of bosses extending transversely from opposite sides of the distal end portion of the second curved leg member.

14. The clip of claim 10, wherein the hinge is integral to the first and second curved leg members, the hinge is resilient, and the hinge includes a continuous concave inner surface and a continuous convex outer surface.

15. A clip for ligating a vessel, the clip comprising:
first and second curved leg members having respective proximal and distal end portions and curved vessel clamping inner surfaces, the proximal end portions being joined by a hinge,
a rib on the first curved leg member extending longitudinally on the curved vessel clamping inner surface of the first curved leg member from the respective proximal end portion to the respective distal end portion, and
first and second rows of teeth extending longitudinally on the curved vessel clamping inner surface of the second curved leg member, the first and second rows of teeth being transversely separated from each other on opposite sides of a centerline of the curved vessel clamping inner surface of the second curved leg member,
wherein the rib is received between the first and second rows of teeth in a closed configuration.

16. The clip of claim 15, further comprising:
a first pair of bosses extending transversely from opposite sides of the distal end portion of the first curved leg member, and
a second pair of bosses extending transversely from opposite sides of the distal end portion of the second curved leg member.

17. The clip of claim 15, wherein the first curved leg member terminates at a distal end in a hook member curved toward the second curved leg member, the second curved leg member terminates at a distal end in a complimentary locking portion to the hook member, and the hook member is configured to deflect about the distal end of the second curved leg member to lock the clip in the closed configuration when the first and second curved leg members are moved to the closed configuration.

18. The clip of claim 15, wherein the teeth of the first row of teeth are longitudinally separated from each other along the curved vessel clamping inner surface of the second curved leg member, and the teeth of the second row of teeth are longitudinally separated from each other along the curved vessel clamping inner surface of the second curved leg member.

19. The clip of claim 15, wherein the hinge is integral to the first and second curved leg members, the hinge is resilient, and the hinge includes a continuous concave inner surface and a continuous convex outer surface.

20. The clip of claim 15, wherein the first and second rows of teeth are staggered along the curved vessel clamping inner surface of the second curved leg member.

21. The clip of claim 15, wherein the curved vessel clamping inner surface of the first curved leg member and the curved vessel clamping inner surface of second curved leg member have matching radii of curvature.

22. The clip of claim 15, wherein each of the first and second curved leg members has a curvature extending from the respective proximal end portion to the respective distal end portion.

23. The clip of claim 15, wherein the curved vessel clamping inner surface of the second curved leg member has a convex radius of curvature facing the first curved leg member, and the curved vessel clamping inner surface of the first curved leg member has a concave radius of curvature facing the second curved leg member.

* * * * *